United States Patent [19]

Lipton

[11] Patent Number: 5,506,231
[45] Date of Patent: Apr. 9, 1996

[54] TREATMENT OF AIDS DEMENTIA, MYELOPATHY AND BLINDNESS

[75] Inventor: Stuart A. Lipton, Newton, Mass.

[73] Assignee: The Children's Medical Center Corporation, Boston, Mass.

[21] Appl. No.: 6,326

[22] Filed: Jan. 21, 1993

Related U.S. Application Data

[63] Continuation-in-part of Ser. No. 571,949, Aug. 23, 1990, abandoned, Ser. No. 939,824, Sep. 3, 1992, Pat. No. 5,334, 618, and Ser. No. 949,342, Sep. 22, 1992, Pat. No. 5,234, 956, which is a continuation of Ser. No. 688,965, Apr. 19, 1991, abandoned, said Ser. No. 571,949, is a continuation-in-part of Ser. No. 502,296, Mar. 30, 1990, Pat. No. 5,053, 419, which is a continuation-in-part of Ser. No. 331,872, Mar. 31, 1989, said Ser. No. 939,824, is a continuation-in-part of Ser. No. 680,201, Apr. 4, 1991, abandoned.

[51] Int. Cl.⁶ .......... A61K 31/44; A61K 31/135; A61K 31/13
[52] U.S. Cl. .......... 514/289; 514/284; 514/647; 514/661; 514/662
[58] Field of Search ............ 514/661, 662, 514/284, 289, 647

[56] References Cited

U.S. PATENT DOCUMENTS

| | | |
|---|---|---|
| 3,328,251 | 6/1967 | Smith. |
| 3,391,142 | 7/1968 | Mills et al.. |
| 3,456,057 | 7/1969 | Cairns et al.. |
| 4,122,193 | 10/1978 | Scherm et al.. |
| 4,148,896 | 4/1979 | Smith et al.. |
| 4,273,774 | 6/1981 | Scherm. |
| 4,351,847 | 9/1982 | Griffith et al.. |
| 4,806,543 | 2/1989 | Choi. |
| 4,812,458 | 3/1989 | Honore et al.. |
| 4,837,218 | 6/1989 | Olney. |
| 5,053,419 | 10/1991 | Lipton .................. 514/356 |
| 5,061,703 | 10/1991 | Bormann et al.. |

FOREIGN PATENT DOCUMENTS

| | | |
|---|---|---|
| 0002065 | 5/1979 | European Pat. Off.. |
| WO/90/11761 | 10/1990 | WIPO. |
| WO/91/02810 | 3/1991 | WIPO. |

OTHER PUBLICATIONS

Merk Index 10th Ed. No. A7, 1983.
Merk Index 10th Ed. No. 8116, 1983.
Merk Index 10th Ed. No. 373, 1983.
Choi et al., J. Pharm. and Exp. Therapeutics 242:713–720 (1987).
Pomerantz et al., New Eng. Med. 317:1643–1647 (1987).
Brenneman et al., Nature 335:639–642 (1988).
Price et al., Science 239:586–590 (1988).
Davenport et al., Eur. J. Pharm. 154:73–78 (1988).
Goldenberg et al., J. Pharm. and Exp. Therapeutics 245:1081–1087 (1988).
Hahn et al., Proc. Nat'l. Acad. Sci. USA 85:6556–6560 (1988).
Ho et al., Annals of Internal Med. 111:400–410 (1989).
Turski et al., Nature 349:414–418 (1989).
Kornhuber et al., European J. Pharm. 166:589–590 (1989).
Borman, European J. Pharm. 166:591–592 (1989).
Aizenman et al., Neuron 2:1257–1263 (1989).
Sernagor et al., Neuron 2:1221–1227 (1989).
Seubert et al., Brain Research 492:366–370 (1989).
Turski Arzneim–Forsch./Drug Res. 40 (I) Nr. 5 (1990).
Müller SCRIP 1515 p. 28 (1990).
Asanaka et al. 112 Chem. Abstract 232458q (1990).
Krieglstein et al., 112 Chem. Abstract 112: 522c (1990).
Nuglisch et al., 113 Chem. Abstract 113: 224453q (1990).
Lipton et al., Neurosci. Abstracts 18:757, No. 321.11, 1992.
Lipton et al. Trends in Neurosci. 15:75–79 (1992).
Lipton et al. Nature 367:113–114 (1994).
Dreyer et al., "HIV–1 Coat Protein Neurotoxicity Prevented by Calcium Channel Antagonists", Science 248:364–367, Apr. 20, 1990.
Lipton et al., Neuron, vol. 7: 111–118, 1991.
Lo et al., Brain Research, "HIV–1 envelope protein evokes intracellular calcium oscillations in rat hippocampal neurons", Brain Research, 594:189–196 (1992).
Perovic et al., "The triaminopyridine flupirtine prevents cell death in rat cortical cells induced by N–Methyl–D–aspartate and gp 120 of HIV–1", Eur. J. of Pharmacol., 228:27–33 (1994).
Müller et al., "gp 120 of HIV–1 induces apoptosid in rat cortical cell cultures: prevention by memantine", Eur. J. of Pharmac., 226:209–214 (1992).
Giulian et al., "The envelope glycoprotein of human immunodeficiency virus type 1 stimulates release of neurotoxins from monocytes", Proc. Natl. Acad. Sci. USA, 90:2769–2773 (1993).
Rytik et al., "Susceptibility of Primary Human Glial Fibrillary Acidic Protein–Positive Brain Cells to Human Immunodeficiency Virus Infection In Vitro . . . ", Aids Res. and Human Retroviruses 7:89–95 (1991).
Brightbart et al., The Lancet 2(8626):1488–1489 (1988).
Meldrum et al., "Excitatory amino acid neurotoxicity and neurodegenerative disease", Trends in Pharmac. Sciences, 11:379–387 (1990).

*Primary Examiner*—Marianne M. Cintins
*Assistant Examiner*—William R. A. Jarvis
*Attorney, Agent, or Firm*—Fish & Richardson

[57] ABSTRACT

Damage to CNS neurons of a human patient infected with a human immunodeficiency virus is reduced by administering an antagonist of the NMDA receptor complex.

17 Claims, 8 Drawing Sheets

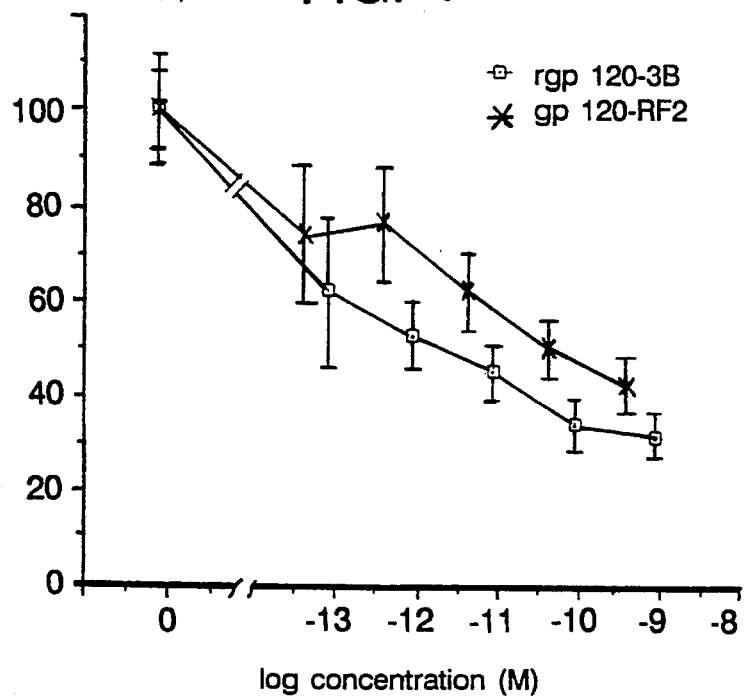
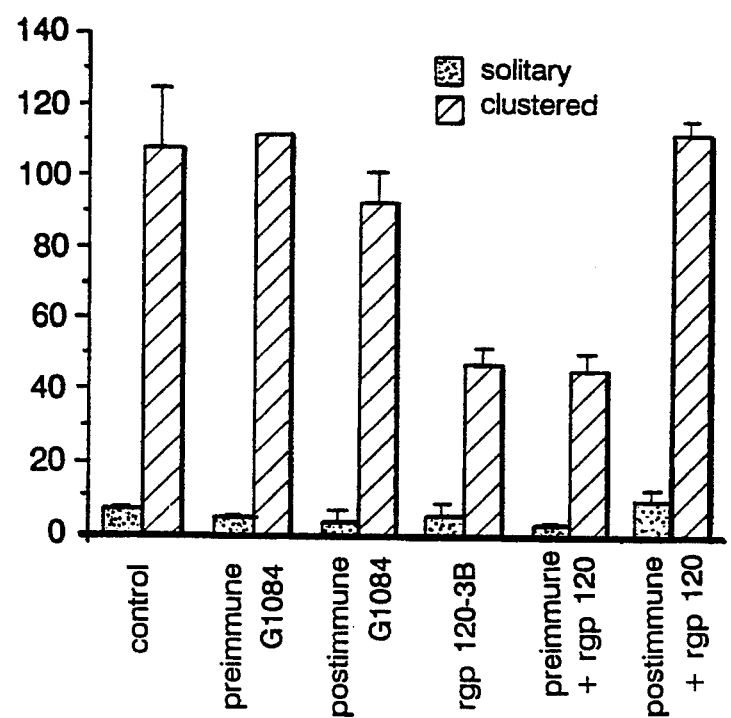

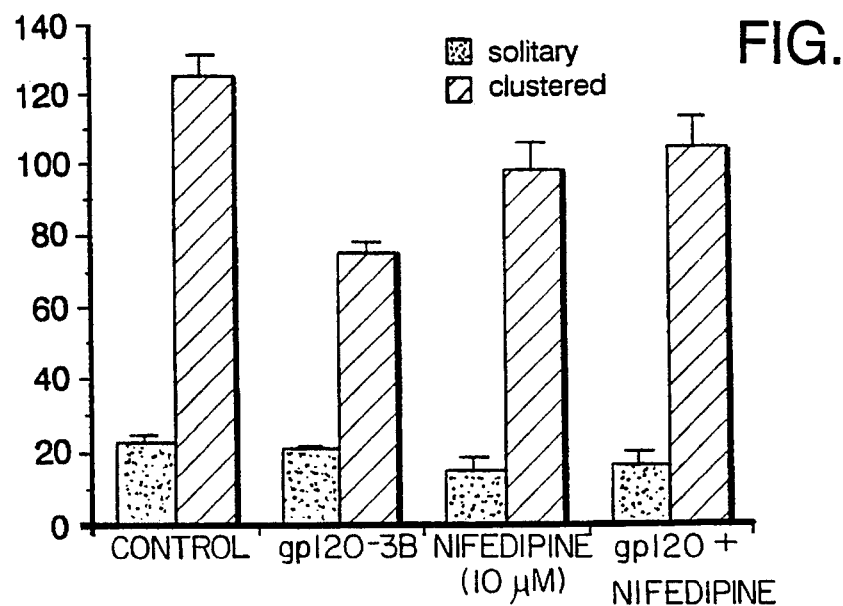
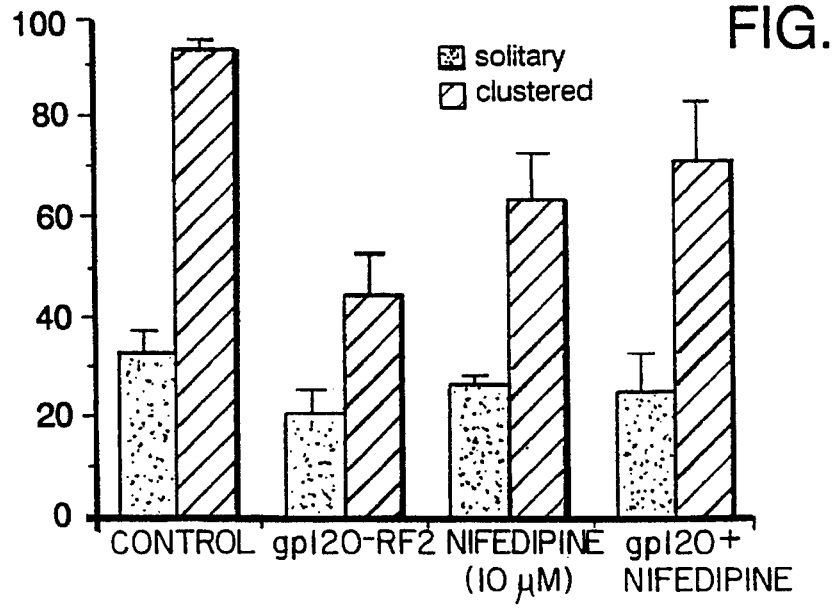

TREATMENT OF AIDS DEMENTIA, MYELOPATHY AND BLINDNESS

This application is a continuation-in-part of the following commonly owned U.S. patent applications:

1. U.S. Ser. No. 07/571,949, filed Aug. 23, 1990 (now abandoned), which was a continuation in part of U.S. Ser. No. 07/502,296, filed Mar. 30, 1990, now issued as U.S. Pat. No. 5,053,419, which in turn was a continuation in part of U.S. Ser. No. 07/331,872, filed Mar. 31, 1989;
2. U.S. Ser. No. 07/939,824, filed Sep. 3, 1992, now issued as U.S. Pat. No. 5,334,618, which was a continuation in part of U.S. Ser. No. 07/680,201, filed Apr. 4, 1991 (now abandoned); and
4. U.S. Ser. No. 07/949,342, filed Sep. 22, 1992, now issued as U.S. Pat. No. 5,234,956, which in turn was a continuation of U.S. Ser. No. 07/688,965 Apr. 19,1991 (abandoned).

U.S. Ser. No. 07/677,365 is hereby incorporated by reference.

BACKGROUND OF THE INVENTION

This invention relates to the treatment of central nervous system (CNS) disorders caused by infection with human immunodeficiency virus (HIV).

HIV infection in humans causes general immunosuppression and involves other disorders, such as myelopathy, vision loss, or a dementing neurological disorder, i.e., the AIDS dementia complex, the latter of which is a common and important cause of morbidity in patients in advanced stages of infection. HIV infection has been documented in various areas of the CNS, including the cerebral cortex, spinal cord, and retina. Price et al. (1988, *Science* 239:586) and Ho et al. (1989, *Annals in Internal Medicine* 111:400) review the clinical, epidemiological, and pathological aspects of the AIDS dementia complex, and suggest that the mechanism underlying the neurological dysfunction may be indirect tissue damage by either viral- or cellular-derived toxic substances released by infected cells. In addition to the previously known white matter lesions present in the brains of patients with AIDS related dementia, there is evidence that approximately 20% of the neurons are damaged or die (Ketzler et al., *Acta Neuropathologica* 80:92, 1990). By HIV we mean to include all types and variants of HIV including HIV-1, HIV-2, LAV, and others.

Pomerantz et al. (1987, *New Eng. J. Med.* 317:1643) document the presence of HIV type I infection of the retina in two patients with AIDS. Brenneman et al. (1988, *Nature* 335:639) found gp120, the coat protein of HIV, in killed hoppocampal neurons.

SUMMARY OF THE INVENTION

One aspect of the invention generally features methods of reducing damage to CNS neurons in a human patient infected with a human immunodeficiency virus by administering to the patient a therapeutic composition comprising compound which is an antagonist of the NMDA receptor-channel complex capable of reducing the gp120-responsive rise in free $Ca^{++}$ ion concentration in the patient's CNS neurons, in a concentration effective to cause such a reduction.

All categories of NMDA receptor complex antagonists can generally be used in accordance with the invention, including the following: competitive NMDA antagonists, acting at the agonist binding site; un-competitive NMDA antagonists, blocking the NMDA channel; NMDA antagonists operating at the glycine site of the NMDA receptor; NMDA antagonists operating at the polyamine site of the NMDA receptor; NMDA antagonists operating at the redox site of the NMDA receptor; and non-competitive NMDA antagonists; inhibitors of NMDA receptor-stimulated protein kinase C activation.

In a second aspect, the invention features methods of reducing damage to CNS neurons in a human patient infected with a human immunodeficiency virus by administering to said patient a therapeutic composition comprising compound which is capable of reducing the gp120-responsive rise in free $Ca^{++}$ ion concentration in said CNS neurons of said patient, in a concentration effective to cause such reduction. In addition to the NMDA receptor complex antagonists mentioned above, and antagonists of the voltage-dependent Ca++ ion channel, e.g., those described in U.S. Pat. No. 5,053,419, hereby incorporated by reference, the invention also features administering other compounds capable of reducing the gp120-responsive rise in free $Ca^{++}$ ion concentration in the patient's CNS neurons, in a concentration effective to cause such a reduction. Such other compounds include competitive glutamate antagonists operating at a non-NMDA glutamate receptor, or non-competitive glutamate antagonists operating at a non-NMDA glutamate receptor, and they include compounds operating at other glutamate receptors such as the metabotropic glutamate receptor, or compound having other mechanisms to decrease intracellular Ca++, such as compounds that are effective to decrease release of glutamate, and compounds that are effective to decrease intracellular Ca++ following glutamate receptor stimulation.

In either aspect of the invention, preferably the patient's blood manifests anti-HIV antibodies and the patient manifests symptoms of AIDS-related complex or of AIDS. Preferably, the compounds are administered orally or intravenously, and they are capable of crossing the blood-brain barrier. Compounds that do not freely cross the blood-brain barrier are less preferred; these may be administered intrathecally to the brain and/or spinal cord or intravitreally to the retina. In the case of compounds that have an intermediate ability to cross the blood-brain barrier, the mode of administration will depend on the dosage required and other factors. In some instances, drugs that are otherwise unable to cross the blood-brain barrier may be able to do so in instances when the barrier has been disrupted by HIV or related infection.

The invention thus involves treating (including prophylactic treatment) or preventing dementia, myelopathy, or vision loss associated with infection by a human immunodeficiency virus.

Other features and advantages of the invention will be apparent from the following description of the preferred embodiments thereof, and from the claims.

BRIEF DESCRIPTION OF THE DRAWINGS

The drawings will first briefly be described. Drawings FIG. 1 is a dose-response curve showing retinal ganglion cell death at different gp120 concentrations;

FIG. 2 is a graph of retinal cell survival in the presence of recombinant gp120 and antiserum;

FIG. 5 is a graph of retinal cell survival in the presence of gp120 and/or 10µM nifedipine;

DESCRIPTION OF THE PREFERRED EMBODIMENTS

Figure 3A:
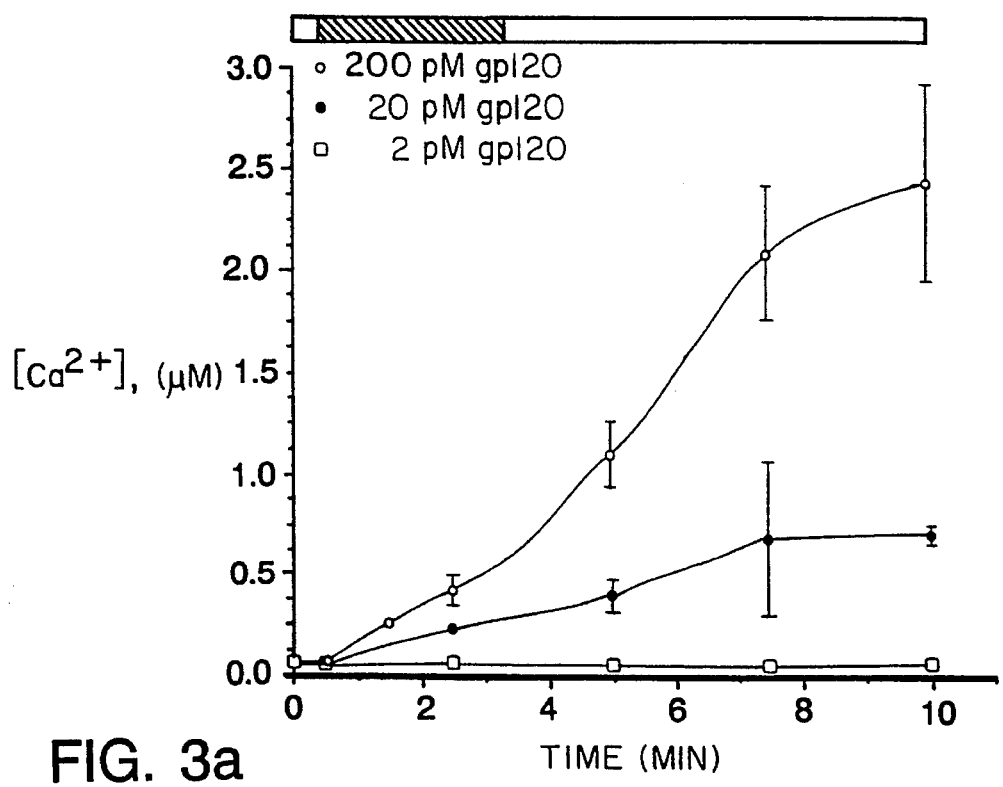
FIG. 3(a) is a graph of kinetics of intracellular free $Ca^{2+}$ concentration ($[Ca^{2+}]i$) in a retinal ganglion cell in response to various doses of glo120, and (b) is a steady state dose-response graph of gp120 concentration versus $[Ca^{2+}]i$.

Selection of Antagonists of the. Voltage Dependent Calcium Channel

Any suitable antagonist, generally, of neuronal voltage-dependent $Ca^{2+}$ channels (Tables 1,2, and 3) may be used to reduce or prevent AIDS-related vision loss, myelopathy, or dementia. Preferred calcium channel antagonists include, but are not limited to, the following drugs, of which the most preferred are those that are capable of crossing the blood-brain barrier, for example, nimodipine (Miles Pharmaceuticals, West Haven, Conn.) Smith Kline drug no. 9512 (Smith Kline, French-Beecham, Philadelphia, Pa.), diproteverine (Smith, Kline, French-Beecham), and flunarizine. Less preferred antagonists are those that are less CNS permeable, for example, verapamil (Calan, G. D. Searle & Co., Chicago, Ill.; Isoptin, Knoll, Whippany, N.J.), nitrendipine, diltiazem (Cardizem, Marion, Kansas City, Mo.), and nifedipine, U.S. Pat. No. 3,485,847, hereby incorporated by reference (Procardia, Pfizer, NY, N.Y.; Adalat, Miles). Other $Ca^{2+}$ channel antagonists which may be useful are mioflazine, flunarizine, bepridil, lidoflazine, CERM-196, R-58735, R-56865, Ranolazine, Nisoldipine, Nicardipine, PN200-110, Felodipine, Amlodipine, R-(–)-202-791, and R-(+)-Bay-K-8644 (Miles, Bayer), whose chemical formulae are described in Boddeke et al., Trends in Pharmacologic Sciences (1989) 10:397 (hereby incorporated by reference) and Triggle et al., Trends in Pharmacologic Sciences (1989) 10:370. Various calcium channel antagonists have been identified (Hosey, J. Membrane Bio. 104:81, 1988; Ohtsuka et al., General Pharmacology 20:539, 1989; Greenberg, Annals Neurol. 21:317, 1987; and Lin et al., Proc. Natl. Acad. Sci. USA 87:4538, 1990; hereby incorporated by reference).

For any given calcium channel antagonist, effectiveness in preventing neurological disorders associated with HIV-1 (or other HIV) infection is determined by screening the drug using one or more of the following assays of neuronal cell function; i.e., neuronal cell death, detection of intracellular free $Ca^{2+}$ ion concentration in neurons, and detection of current flow through $Ca^{2+}$ channels. An effective antagonist will cause a decrease in HIV-1-associated neuronal cell damage or death, and will prevent the rise in intracellular $Ca^{2+}$ ion concentration that occurs in the presence of gp120. In addition, an effective antagonist will decrease $Ca^{++}$ ion influx through neuronal calcium channels to a degree sufficient to reduce neuronal cell death, while not completely blocking $Ca^{++}$ ion influx, an event which itself might kill neuronal cells. The antagonist may be compounded into a pharmaceutical preparation, using pharmaceutical compounds well-known in the art; the exact formulation of the antagonist compound depends upon the route of administration.

TABLE 1

Antagonists of the Voltage Dependent Calcium Channels (N, L, T, P and other types)

dihydropyridines (e.g., nimodipine)
phenylalkylamines (e.g., verapamil, (S)-emopamil, D-600, D-888)
benzothiazepines (e.g., diltiazem and others)
bepridil and related drugs
diphenylbutylpiperdines
diphenylpiperazines (e.g., flunarizine/cinnarizine series)
HOE 166 and related drugs
fluspirilene and related drugs
toxins and natural compounds (e.g., snail toxins -
ωconotoxin GVIA and GVIIA, maitotoxin, taicatoxin,
tetrandine, hololena toxin, plectreurys toxin,
funnel-web spider venom and its toxin fraction,
agatoxins including ω-agatoxin IIIA and ω-agatoxin IVA.

TABLE 2

DIHYDROPYRIDINE CALCIUM CHANNEL ANTAGONISTS

| | |
|---|---|
| nifedipine | KW3049 |
| niludipine | oxodipine |
| PY108-068 (darodipine) | CD349 |
| mesudipine | TC81 |
| GX 1048 | YM-09730-5 or (4S)DHP |
| floridine | MDL72567 |
| nitrendipine | Ro18-3981 |
| nisoldipine | DHP-218 |
| nimodipine | nilvadipine |
| nicardipine | amlodipine |
| felodipine | 8363-S |
| PN200-110 (Isradipine) | iodipine |
| CV4093 | azidopine |

TABLE 3

OTHER CALCIUM CHANNEL ANTAGONISTS

| | |
|---|---|
| diclofurime | D-600 |
| pimozide | D-888 |
| prenylamine | Smith Kline 9512 |
| fendiline | ranolzine |
| perhexiline | lidoflazine |
| mioflazine | CERM-11956 |
| flunarizine/cinnarizine series | R-58735 |
| | R-56865 |
| verapamil | amiloride |
| dilfiazine | phenytoin |
| dipropervine | thioridazine |
| (S)-emopamil | tricyclic antidepressents |

Selection of Anagonists of the NMDA Receptor-Channel Complex

Any suitable antagonist of the N-methyl-D-aspartate (NMDA) subtype of glutamate receptor-channel complex may be used to reduce or prevent AIDS-related vision loss, myelopathy, or dementia. The antagonist can be a channel blocker, a receptor antagonist, or act at the glycine co-agonist site or at any of several modulation sites such as the Zinc site, the Magnesium site, or the polyamine site. (Table 4). Many antagonists of the NMDA receptor have been identified (Watkins et al., Trends in Pharmacological Sci 11:25, 1990, hereby incorporated by reference). Other substances that interact with the NMDA receptor-channel complex in a manner that attenuates the gp120-responsive rise in intracellular $Ca^{2+}$ ion concentration may also be used in the method of the invention. Such modulatory substances include those known to cause oxidation of the redox site of the NMDA receptor (U.S. Ser. No. 391,778, filed Aug. 9, 1989, and incorporated herein by reference), and oxidized or reduced glutathione.

TABLE 4

| NMDA Antagonists | NMDA Antagonists | NMDA Antagonists |
|---|---|---|
| 1. Competitive NMDA Antagonists (act at agonist binding site) CGS-19755 (CIBA-GEIGY) and other piperdine derivatives, D-2-amino-5-phosphovalerate, D-2-amino-7-phosphonoheptanoate (AP7) CPP {[3-(2-carboxypiperazin-4-y-propyl-1-phosphonic acid]} | 2. Channel Blockers (Un-Competitive NMDA Antagonists) MK-801 (Dizocilpine) and other derivatives of dibenzyocycloheptene (Merck) Sigma receptor ligands, e.g. Dextrorphan, dextromethorphan and morphinan derivatives (Hoffman La Roche) such as caramiphen and rimcazole (which also block calcium channels) | 3. Antagonists at Glycine Site of the NMDA Receptor Kynurenate, 7-chloro-kynurenate, 5,7-chloro-kynurenate, thio-derivatives, and other derivatives. (Merck) Indole-2-carboxylic acid |
| LY274614, CGP39551, CGP37849, LY233053, LY233536 O-phosphohomoserine MDL100,453 | Ketamine, Tiletamine and other cyclohexanes Phencyclidine (PCP) and derivatives, and pyrazine compounds Memantine, amantadine, rimantadine and derivatives CNS 1102 (and related bi- and tri-substituted guanidines) Diamines Conantokan peptide from *Conus geographus* Agatoxin-489 | DNQX Quinoxaline or oxidiazole derivatives including CNQX, NBQX Glycine partial agonist (e.g. Hoecht-Roussel P-9939) |
| 4. Polyamine Site of NMDA Receptor Arcaine and related biguanidines and biogenic polyamines Ifenprodil and related drugs Diethylenetriamine SL 82,0715 1,10-diaminodecane (and related inverse agonists) | 5. Redox Site of NMDA Receptor Oxidized and reduced glutathione PQQ (pyrroloquinoline quinone) Compounds that generate Nitric Oxide (NO) or other oxidation states of nitrogen monoxide (NO+, NO−) including those listed in the box below Nitroglycerin and derivatives, Sodium Nitroprusside, and other NO generating listed on p. 5 of this table Nitric oxide synthase (NOS) Inhibitors listed on p. 6 of this table Flavin Inhibitors: diphenyliodimium; Calmodulin inhibitors, trifluoperizine Calcineurin Inhibitors, e.g., FK-506 (inhibits calcineurin and thus NOS diphosphorylase) cyclosporin A, and analogs including rapamycin Lipoic acid and lipoate Superoxide dismutase; catalase and other compounds blocking steps in the process of formation of Arg—No. or ONO. | 6. Other Non-competitive NMDA Antagonists Hoechst 831917189 SKB Carvedilol |
| Inhibitors of Downstream Effects of NMDA | Inhibitors of Downstream Effects of NMDA | Non-NMDA Receptor Antagonists |
| 7. Agents to inhibit protein kinase C activation by NMDA stimulation (involved in NMDA toxicity) MDL 27,266 (Merrill Dow) and triazole-one derivatives Monoxialoganglioxides (eg GM1 of Fidia Corp.) and other ganglioxide derivatives LIGA20, LIGA4 (may also effect calcium extrusion via calcium ATPase) | 8. Downstream effects from Receptor Activation 8a. To decrease phopshatidylinositol metabolism kappa opioid receptor agonist: U50488(Upjohn) and dynorphan kappa opioid receptor agonist: PD117302, CI-977 8b. To decrease hyddrogen peroxide and free radical injury, eg antioxidants 21-aminosteroid (lazaroids) such as | 9A. Non-NMDA antagonists (Competitive) CNQX, NBQX, YM900, DNQX, PD140532 AMOA (2-amino-3[8-9carboxymethoxyl-5-methoxylisoxazol-4-yl]propionate] 2-phosphophonoethyl phenylalamine derivatives, i.e. 5-ethyl, 5-methyl, 5-trifluoromethyl 9B. Non-NMDA Non competitive |

TABLE 4-continued

| | | |
|---|---|---|
| | U74500A, U75412E and U74006F U74389F, FLE26749, Trolox (water soluble alpha tocophenol), 3,5-dialkoxy-4-hydroxy-benzylamines | antagonists GYKI52466 |
| | Compounds that generate Nitric Oxide (NO) or other oxidation states of nitrogen monoxide (NO+, NO−) including those listed in the box below Nitroglycerin and derivatives, Sodium Nitroprusside, and other NO generating listed on p. 5 of this table Nitric oxide synthase (NOS) Inhibitors: Arginine analogs including N-mono-methyl-L-arginine (NMA); N-amino-L-arginine (NAA); N-nitro-L-arginine (NNA); N-nitro-L-arginine methyl ester; N-iminoethyl-L-ornithine | Evans Blue |

| Agents Active at Metabotrop Glutamate Receptors | Decrease glutamate release | Drugs to decrease intracellular calcium following glutamate receptor stimulation |
|---|---|---|
| 10a. Blockers of Metabotropic Glutamate Receptors AP3 (2-amino-3-phosphonoprionic acid)<br><br>10b. Agonists of Metabotropic Glutamate Receptors (1S, 3R)-1-Amino-cyclopentane-1,3-dicarboxylic acid [(1S, 3R)-ACPD], commonly ref as 'trans'-ACPD | 11. Agents to decrease glutamate release<br><br>Adenoxine, and derivatives, e.g. cyclohexyladenoxine CNS1145<br><br>Conopeptides: SNX-111, SNX-183, SNX-230<br><br>Omega-Aga-IVA, toxin from venom of funnel web spider Compounds that generate Nitric Oxide (NO) or other oxidation states of nitrogen monoxide (NO+, NO−) including those listed in the box below Nitroglycerin and derivatives, Sodium Nitroporoxide, and other NO generating listed on p. 5 of this table Nitric oxide synthase (NOS) Inhibitors: Arginine analogs including N-mono-methyl-L-arginine (NMA); N-amino-L- | 12a. Agents to decrease intracellular caclium release Dantrolene (sodium dantrium); Ryanodine (or ryanodine + caffiene) 12b. Agents inhibiting intracellular Calcium-ATPase Thapsigargin, cyclopiazonic acid, BHQ ([2,5-di-(tert butyl)-1,4-benzohydroquinone; 2,5-di-(tert-butyl)-1,4benzohydroquinone]) |
| arginine (NAA); N-nitro-L-arginine (NNA); N-nitro-L-arginine methyl ester, | N-iminoethyl-L-ornithine Additional NO-generating compounds Isosorbide dinitrate (isordil) S-nitrosocaptopril (SnoCap) Serum albumin coupled to nitric oxide (SA—NO) Cathepsin coupled to nitric oxide (cathepsin—NO) Tissue plasminogen activator coupled to NO (TPA—NO) Ion-nitrosyl complexes (e.g., nitrosyl-iron complexes, with iron in the Fe2+ state) Nicorandil Arginine analogs including N-mono-methyl-L-arginine (NMA) N-amino-L-arginine (NAA) N-nitro-L-arginine (NNA) N-nitro-L-arginine methyl ester N-iminoethyl-L-ornithine Diphenylene iodonium and analogs See, Steuhr, FASB 5:98–103 (1991) | |

Assays for Neuronal Cell Function and Death

An antagonist may be tested for utility in the method of the invention using various types of neuronal cells from the central nervous system, using the following assays, as long as the cell can be isolated intact using conventional techniques. Retinal cultures were used in the following assays (but hippocampal cortex neurons have also been used, e.g., in assays of neuronal death and intracellular calcium), because they can be produced from postnatal mammals, are well-characterized, and contain a central neuron, the retinal ganglion cell, that can be unequivocally identified with fluorescent labels. A substantial portion of retinal ganglion cells in culture display both functional synaptic activity and bear many, if not all, of the neurotransmitter receptors found in the intact retina.

Retinal ganglion cells from postnatal rats were identified and their viability ascertained as follows. Under general anesthesia, the fluorescent dye granular blue (Mackromolekulare Chemic, Umstadt, FRG) was injected as approximately a 2% (w/v) suspension in saline into the superior colliculus of 4- to 7-day-old Long Evans rats (Charles River Laboratory, Wilmington, Mass.). Two to 7 days later, the animals were killed by decapitation and enucleated, and the retinas quickly removed. The retinas were dissociated and cultured in Eagle's minimum essential medium (MEM, catalog #1090, Gibco Grand Island, N.Y.), supplemented with 0.7% (w/v) methylcellulose, 2 mM glutamine, 1 µg/ml gentamicin, 16mM dextrose, and 5%(v/v) rat serum, as described in Lipton et al., 1987, J. Physiol. 385:361. The cells were then plated onto 75 mm$^2$ glass coverslips coated with poly-L-lysine in 35 mm tissue culture dishes; gp120 was then added. Sibling cultures received various doses of gp120, gp120 plus $Ca^{2+}$ channel antagonists or NMDA receptor-channel complex antagonists, or no drugs at all.

Cell survival was assayed after one day in culture. Incubations lasted 20–24 h at 37° C. in an atmosphere of 5% $CO_2$/95% air. Ganglion cells could be unequivocally identified by the continued presence of the fluorescent blue dye. The ability of retinal ganglion cells to take up and cleave fluorescein diacetate to fluorescein was used as an index of their viability as described in detail in Hahn et al., 1988, suprs. Dye uptake and cleavage correlates well with normal electrophysiological properties assayed with patch electrodes.

To perform the viability test, the cell-culture medium was exchanged for physiological saline containing 0.0005% fluorescein diacetate for 15–45 s, and then cells were rinsed in saline. Retinal ganglion cells that did not contain the fluorescein dye (and thus were not living) often remained visible under both phase-contrast and UV fluorescence optics, the latter because of the continued presence of the marker dye granular blue; other dead retinal ganglion cells had disintegrated and only debris remained. In contrast, the viable retinal ganglion cells displayed not only a blue color in the UV light but also a yellow-green fluorescence with filters appropriate for fluorescein. Thus, the use of two exchangeable fluorescence filter sets permitted the rapid determination of viable ganglion cells in the cultures, which were found as solitary neurons or lying among other cells in small clusters (usually in the ratio of approximately 1:10 solitary to clustered).

Production and Purification of gp120

Two native isolates of gp120, RF2 and 3B, obtained from (Brenneman et al., 1988, Supra; Nature 335:445; National Cancer Institute, Fredrick, Md.) were purified by immunoaffinity chromatography, as described by Robey et al. (1986, Proc. Nat. Aca. Sci. 83:7023), Pyle et al. (1988, AIDS Res. Hum. Retrovir. 3:387), and Kornfeld et al.(1988, supra). In addition, recombinant gp120 derived from the gene encoding gp120-3B, was obtained as follows.

Recombinant gp120 was produced by transfection of a Chinese Hamster Ovary (CHO) cell line (ATCC) with a plasmid containing isolate 3B envelope coding sequences encoding amino acids 61–531 (Lasky et al., 1986, Science 233:209). The gene was truncated to remove the native amino-terminal signal sequence and the carboxy-terminal transmembrane domain, and then ligated in-frame to the herpes simplex virus glycoprotein-D signal sequence (Berman et al., 1985, Science 227:1490) to allow the envelope protein to be constituitively secreted by the CHO cell line. Production in a mammalian cell ensured that the envelope protein was glycosylated. This envelope glycoprotein, rgp120-3B, was purified by immunoaffinity chromatography to 5 parts in a million (99.995%) pure based on estimates from polyacrylamide gel electrophoresis and Western blotting. The preparations of gp120 (at low concentrations) were highly labile in that they had to be freshly thawed (with refreezing avoided) in order to display activity.

gp120 Increases Neuronal Cell Death In Vitro

Neuronal cell death was assayed by incubating retinal ganglion cells in vitro with purified native or recombinant gp120 and scoring live cells.

FIG. 1 is a dose-response curve for concentrations of gp 120 ranging from $10^{-9}$ M to less than $10^{-13}$ M, and shows that incubation of native purified gp120 (RF2) or recombinant gp120 preparations with cultured retinal cells resulted in the death of a significant number of ganglion cells within 24 h. A significant increase (P<0.01) in cell death was observed at gp120 concentrations above $2 \times 10^{-12}$M. Living cells were scored without knowledge of treatment in each culture. Control cultures had counts ranging from 95 to 250 retinal ganglion cells per 75 mm$^2$ coverslip, which corresponds to approximately 1% of the total retinal cell population. Each point was determined in at least triplicate in each experiment, and the data represent 3 experiments. Values shown are means +/− their standard errors. Statistical analysis consisted of a one-way analysis of variance followed by a Scheffe multiple comparison of means. These results indicate that neuronal cell death in this experiment was due to the addition of gp120. To confirm this result, a control experiment was done in which neuronal cell death was prevented by the addition of antiserum specific for the gp120 envelope protein.

gp120 Antiserum Prevents gp120-Associated Neuronal Cell Death

Goat anti-gp120 immune sera were prepared by primary and secondary intramuscular immunizations of recombinant fragments of the 3B isolate of gp120 plus Freund's adjuvant. Prior to these injections, preimmune serum was collected from each goat. The presence of gp120 antibodies in the postimmune serum was verified by polyacrylamide gel electrophoresis of immunopurified gp120 and Western blotting.

FIG. 2 shows that anti-gp120 antisera prevent neuronal cell killing of rat retinal ganglion cells by recombinant envelope protein (rgp120-3B). Retinal cultures from 8 day-old rats were plated in the presence or absence of 20 pM gp120 plus either postimmune serum containing polyclonal gp120 antibodies from goat G1084, or preimmune serum from the same goat. Sera were used at a concentration of 1:500 diluted in control growth medium. FIG. 2 represents data from 5 separate assays. Error bars represent standard error of the mean. Statistical analysis was performed as described above. The results show that anti-gp120 neutralizes the effect of purified preparation of gp120; that is, cell death in cultures treated with 20 pM gp120 could be prevented by the addition of goat anti-gp120 serum to the culture medium. Neither the antibody preparation or its preimmune serum alone significantly affected survival compared to that observed in control culture medium. In contrast, the addition of gp120 or gp120 plus preimmune serum resulted in significant killing of retinal ganglion cells ($P<0.01$). Furthermore, compared to cultures treated with gp120 alone or gp120 plus preimmune serum, the anti-gp120 serum saved a significant proportion of retinal ganglion cells exposed to gp120 ($P<0.01$). Treatment with antiserum G1084 in the presence of gp120 resulted in neuronal cell counts that were not statistically different from cultures incubated in control medium alone. These figures present results for both solitary and clustered cells in culture; however, the most germane results are those for clustered cells, since neurons are interconnected in the brain.

Measurement of Intracellular $Ca^{2+}$

The concentration of intracellular free $Ca^{2+}$ ($[Ca^{2+}]i$) was measured in postnatal rat retinal ganglion cells and hippocampal neurons by digital imaging microscopy with the $Ca^{2+}$ sensitive fluorescent dye fura 2, as follows. Retinal ganglion cells were cultured from 1-to 2-week-old Long Evans rats as described (Leifer, et al., *Science* 224:303, 1984; Lipton et al., *J. Physiol.* 385:361, 1987. The ganglion cells were identified by the presence of retrogradely transported red fluorescent dyes (DiI or rhodamine-labeled microspheres) or by morphological and immunofluorescence criteria (e.g., the large or α-like ganglion cells stain with neurofilament antibodies; Dräger et al., *Nature* 309:624, 1984). During $Ca^{2+}$ measurements, unless otherwise stated the fluid bathing the neurons consisted of Hanks' balanced salts; 136.7 mMNaCl, 1 mM $NaHCO_3$, 0.34 mM $Na_2HPO_4$, 0.44mM $KH_2PO_4$, 5.36 mM KCl, 2.5 mM $CaCl_2$, 0.5 mM $MgSO_4$, 0.5 mM $MgCl_2$, 5 mM Hepes NaOH, 22.2 mM glucose, and phenol red indicator (0.001% v/v); pH 7.2. Coat protein gp120 and other substances were usually applied to the neurons by pressure ejection after dilution in this bath solution. High $K^+$ solutions were prepared by substituting KCl for NaCl. Neuronal $[Ca^{2+}]i$ was analyzed with fura 2-acetoxy-methyl ester (AM) as described [Grynkiewicz, et al., *J. Biol. Chem.* 260, 3440 (1985); Williams et al., *Nature* 318, 558 (1985); Connor et al., *J. Neurosci.* 7, 1384 (1987); Connor et al, *Science* 240, 649(1988); Cohan et al., *J. Neurosci.* 7, 3588 (1987); Mattson, et al., ibid, 9, 3728 (1989)]. After adding Eagle's minimum essential medium containing 10 μM fura 2-AM to retinal or hippocampal cell neurons, the cultures were incubated at 37° C. in a 5% $CO_2$/95% air humidified chamber and then rinsed. The dye was loaded, trapped, and deesterified within 1 hour, as determined by stable fluorescence ratios and the effect of the $Ca^{2+}$ ionophore ionomycin on measured $[Ca^{2+}]$. During $Ca^{2+}$ imaging, the cells were incubated in a solution of Hepes-buffered saline with Hanks' balanced salts. The $[Ca^{2+}]i$ was calculated from ratio images that were obtained by measuring the fluorescence at 500 nm that was excited by 350 and 380 nm with a DAGE MTI 66 SIT camera mounted on a Zeiss Axiovert 35 microscope. Exposure time for each picture was 500 ms. Analysis was performed with a Quantex (Sunnyvale, Calif.) QX7-210 image-processing system since cells were exposed to ultraviolet light only during data collection (generally less than a total of 20 s per cell), bleaching of fura 2 was minimal.

gp120 Affects the Intracellular Concentration of $Ca^{2+}$

Gp120-promoted neurotoxicity was shown to involve an increase in intracellular $Ca^{2+}$ concentration in the following experiment. Inracellular $Ca^{2+}$ was measured as described above. Application of 200 pM of highly purified gp120 from a recombinant source, as described above, produced a striking increase in a $[Ca^{2+}]i$ (FIG. 3). Compared to control levels ($Ca^{2+}$ =63 ±4 nM, mean ± SEM, n= 42) obtained before the addition of coat protein, levels increased 33-fold within 7 min of gp120 application (2100±330 ruM, n =10; range of values 934 to 3943 nM). Other preparations of gp120 purified from natural isolates (RF2 and 3B) produced similar results. All experiments shown here used the highly purified recombinant gp120.

Similar effects were seen when gp120 was applied to hippocampal neurons. Hippocampal cortices of embryonic day 18 CD rats were dissociated with trypsin (0.027% w/v) and plated at a density of 600,000 cells per 35-mm culture dish, each dish containing five poly-L-lysine-coated glass coverslips. Growth medium (Rosenberg et al, *Neurosci., Lett.*, 103:162, 1989) was changed three times per week. In these experiments, $Ca^{2+}$ measurements were made after 14 to 21 days in culture. Overall, 200 pM gp120 produced an increase in $[Ca^{2+}]i$ in 76% of the neurons tested (n=75).

Several experiments indicated that gp120 was responsible for this rise in $[Ca^{2+}]i$. Application of normal bathing medium did not produce a change in $[Ca^{2+}]i$, although subsequent addition of gp120 to the same retinal ganglion cell neurons increased $[Ca^{2+}]i$ to ~2μM (n=10). Treatment of gp120 with trypsin followed by neutralization with soybean trypsin inhibitor (Sigma Chemical Co.) resulted in a preparation that was no longer active in increasing $[Ca^{2+}]i$. As the recombinant gp120 was produced from a construct with the herpes simplex virus glycoprotein D signal sequence, we applied glycoprotein D, made in exactly the same medium as recombinant gp120, to retinal ganglion cells. Glycoprotein D exerted either no effect or resulted in a modest increase in $[Ca^{2+}]i$ (<200 nM, n=6), but never to the micromolar level typically observed after the addition of equimolar gp120.

Pressure ejection of 50 mMKCl on these neurons yielded an increase in $[Ca^{2+}]i$ to the range of 600 nM (600±99 nM, n=5). Brief exposures to KCl for 30 s to 3 min produced these levels of $Ca^{2+}$ which peaked within 1.5 min of the beginning of the addition and recovered to levels of ~250 nM over the next few minutes (240±21 nM, n=5). In contrast, at least a 1 min addition of 200 pM gp120 was necessary to produce any rise in $[Ca^{2+}]i$, and the effect was persistent and irreversible during the course of an experiment on a single cell (10 to 30 min of $[Ca^{2+}]i$ monitoring, with measurements every 30 s). The time course of the change in $[Ca^{2+}]i$ evoked by a 3 min application of various doses of gp120 is shown in FIG. 3A. The peak level was reached ~7 min after the beginning of the addition. Thus, there were both qualitative and quantitative differences in the observed increase in $[Ca^{2+}]i$ in response to $K^+$ as opposed to gp120.

Figure 3B:
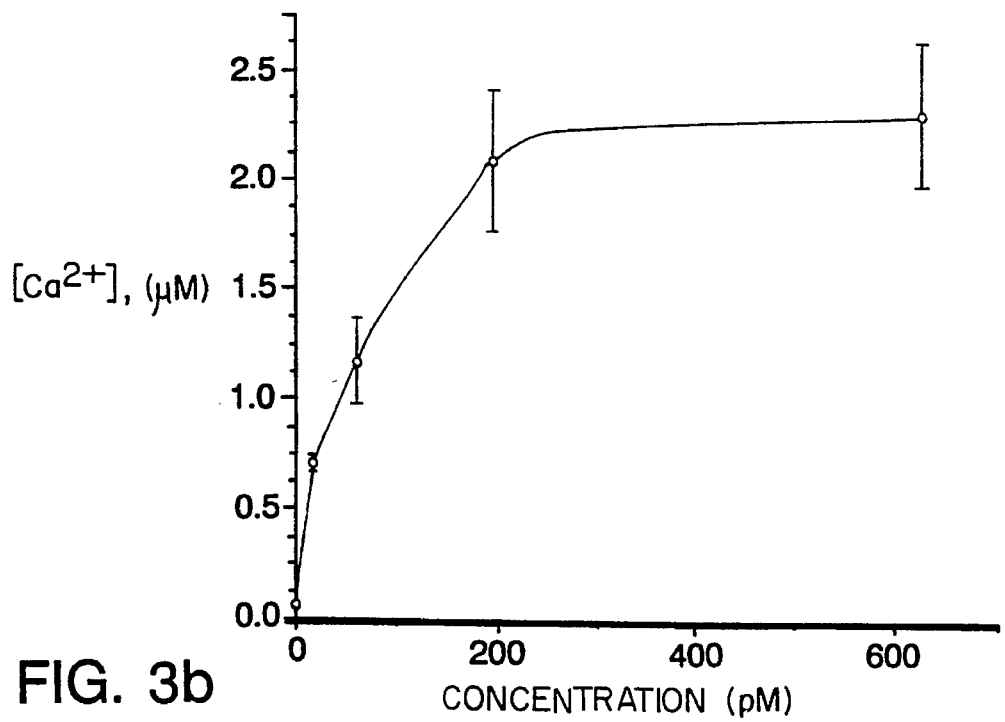

Extremely low doses of gp120, in the picomolar range, were effective in increasing $[Ca^{2+}]i$ in a graded, dose-dependent fashion (FIG. 3B). As little as 20 pM gp120 produced increases in $[Ca^{2+}]i$. Very high levels of free $Ca^{2+}$ ($\geq 2$ μM) were obtained with concentrations of gp120 at or above 200 pM.

The increases in $[Ca^{2+}]i$ observed with gp120 could still have been caused by a contaminant in the purified preparation of the vital envelope protein, although this seems unlikely with the highly purified recombinant gp120. As additional confirmation, we performed immunoprecipitation experiments with goat antibody to gp120 (anti-gp120) coupled to protein A-coated Sepharose beads.

Immunoprecipitation of gp120 was performed as described above with some modifications. A 1:100 or 1:500 dilution of anti-gp120 or preimmune serum from the same goat, was bound to protein-A-coated Sepharose beads, washed, and incubated with a solution containing 7 nM gp120 for 18 hours at 4° C.; this was followed by centrifugation. The supernatant of the material treated with preimmune serum had gp120 activity as evidenced by immunoblotting and by producing an increase in [$Ca^{2+}$]i and cell death (after a dilution of 1:350 to ~20 pM); the material exposed to anti-gp120 had little or no activity.

Figure 4:
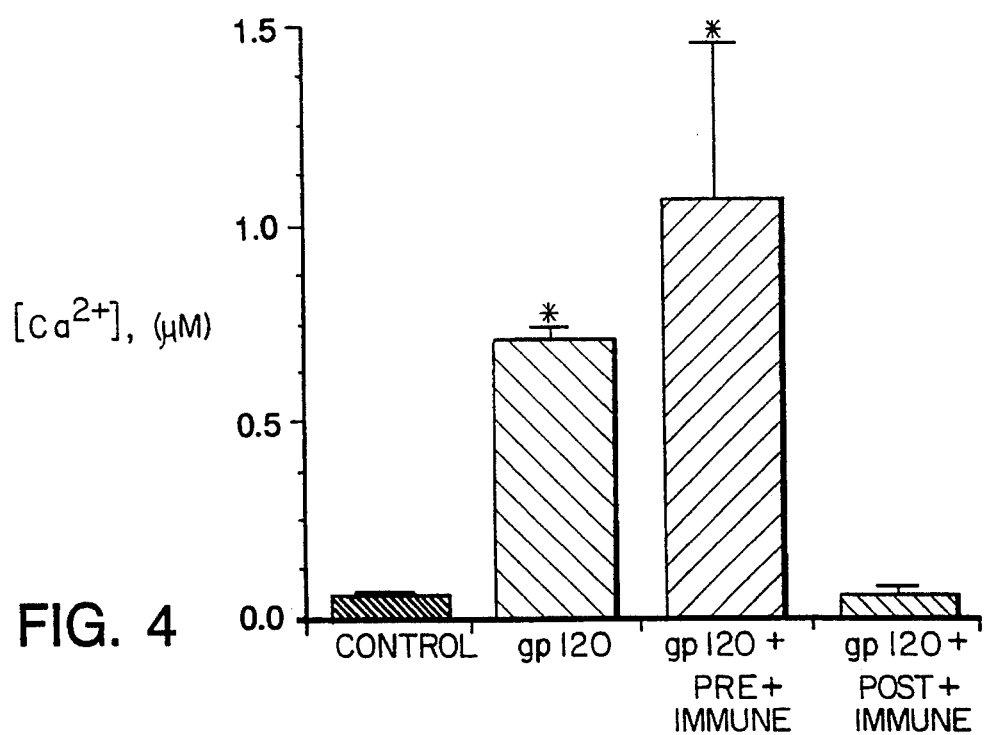
FIG. 4 is a bar graph of gp120-promoted rise in $[Ca^{2+}]i$ in the presence of gp120 alone or gp120 that has been immunoprecipitated with gp120 antiserum.

One of three such experiments is shown in FIG. 4. Treatment with preimmune serum did not significantly alter the ability of gp120 to increase [$Ca^{2+}$]i (compare striped and grey bars; although the mean [$Ca^{2+}$]i was greater after application of gp120 treated with preimmune serum than after gp120 alone, this difference did not reach statistical significance). Both gp120 and preimmune serum-treated gp120 produced a significant increase in [$Ca^{2+}$]i compared to the control ($P<0.01$, analysis of variance (ANOVA) followed by Scheffe multiple comparison of means; significance indicated by an asterisk). In contrast, immunoprecipitation with postimmune serum containing anti-gp120 completely abrogated the gp120 effect.

gp120-Promoted Neuronal Cell Death is Antagonists of the Voltage Dependent Calcium Channel Nifedipine (500nM –10μM) antagonizes the lethal effect of native gp120 isolates 3B and RF2 on retinal ganglion cells. Cell death was quantitated as described above. Cultures received gp120 (20pM) and/or nifedipine (10 μM) at the time of plating, and neuronal cell survival was assayed one day later (FIG. 5). Each value is the mean obtained in 4 replicate tissue culture dishes. Survival of clustered retinal ganglion cells in the control group was significantly greater than those treated with gp120 ($P<0.01$). Compared to gp120-treated cultures, the addition of nifedipine significantly increased retinal ganglion cell survival ($P<0.01$). In comparison to the controls, exposure to 10 μM nifedipine alone resulted in cell death ($P<0.05$), although it was not to the same extent as that observed with gp120 alone. Moreover, in 20 of 22 trials, similar experiments revealed an increase in retinal ganglion cell survival with gp120 plus nifedipine treatment in comparison to gp120 alone, including 3B and RF2 natural isolates and the recombinant 3B form (significant at $P<0.001$, Sign test).

As shown in FIG. 5a, when 10 μM nifedipine was added with gp120-3B to the culture medium at the time of incubation, there was a significant decrease in neuronal killing compared to cultures treated with gp120-3B alone. Nifedipine attenuated neuronal death due to another purified isolate of gp120, RF2, in a similar fashion (FIG. 5b). Interestingly, this preventive effect occurred in spite of the fact that in 5 of 6 experiments (each with triplicate or quadruplicate samples), 10 μM nifedipine induced significant killing on its own compared to controls; in fact, in all six experiments, gp120 and nifedipine-treated culture dishes had somewhat higher levels of survival than that observed with nifedipine alone ($P<0.05$, Sign test). One possible explanation for these phenomena invokes the hypothesis that there is an optimal level of intracellular $Ca^{2+}$ necessary for neuronal health and welfare. Too little $Ca^{2+}$ may inhibit survival (as seen here in the presence of nifedipine) while too much $Ca^{2+}$ may also lead to cell death (as evidenced by the effect of gp120 on $Ca^{2+}$ current). In between these two extremes (the "control" value of $Ca^{2+}$, or the $Ca^{2+}$ concentration in the presence of gp120 + nifedipine), survival may be enhanced. Alternatively, nifedipine alone could be toxic to these neurons for some other, unrelated reason, although in that case it would be difficult to explain the finding that survival was slightly better with the combination of gp120 plus 10 μM nifedipine compared to 10 μM nifedipine alone.

Figure 6A:
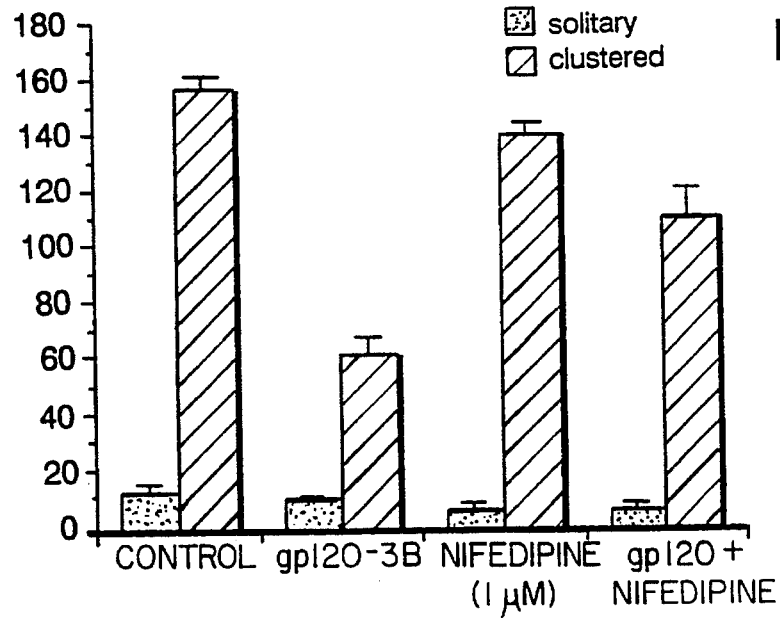
FIG. 6 is a graph of retinal cell survival in the presence of gp120 and/or 1 µM nifedipine or nimodipine.

The effect of using lower doses of calcium channel antagonists on neuronal survival following gp120 treatment is shown in FIG. 6. In FIG. 6a, a lower dosage (1 μM) of nifedipine antagonizes the lethal effect of gp120 (20 pM) without substantial depression of retinal ganglion cell survival by the calcium channel antagonist itself. Treated cultures received gp120-3B (20 pM) and/or nifedipine (1 μM) at the time of plating, and retinal ganglion cell survival was assayed one day later. Incubation with gp120 resulted in neuronal cell killing compared to control sibling cultures ($P<0.01$). The presence of 1 μM nifedipine alone had substantially less detrimental influence on retinal ganglion cell survival than 10 μM (as observed in FIG. 5). Therefore, by fine tuning the dose-response curve, it is possible to find an optimal level of calcium channel antagonist that produces minimal death on its own and yet substantially blocks the toxicity produced by gp120.

Figure 6B:
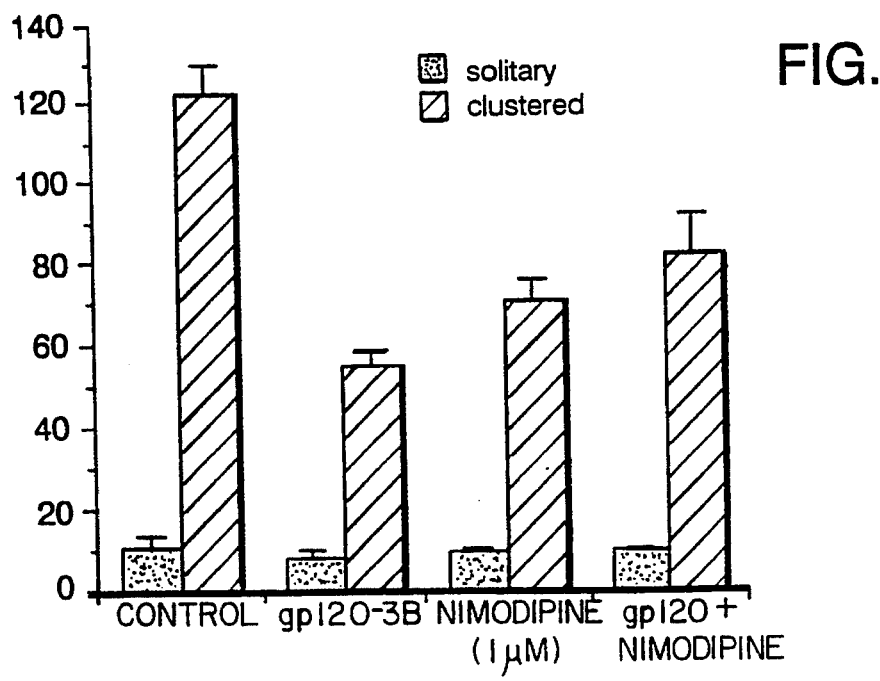

Therapeutic options for decreasing neuronal cell death due to HIV-I infection should include the use of other specific calcium channel antagonists, e.g., nimodipine, which has better CNS permeability than nifedipine (Allen et al., *New Eng. J. Med.* 308:619, 1983). FIG. 6b shows that treatment with 1 μM nimodipine significantly saved clustered retinal ganglion cells from gp120-induced death ($P<0.01$); however, 1 μM nimodipine produced killing by itself similar to that observed with 10 μM nifedipine (FIG. 5). FIG. 6a shows that lowering the concentration of nifedipine to 1 μM also resulted in a decrease in gp120-induced cell death; and, at this concentration, treatment with nifedipine alone did not result in neuronal cell killing. Taken together, the results with nifedipine and nimodipine demonstrate that the dosage of calcium channel blockers is obviously an important parameter; too high a concentration appears to harm normal neurons in the absence of gp120.

Antagonists of the Voltage Dependent Calcium Channel Block the Rise in Intracellular [$Ca^{2+}$] Produced by gp120

Figure 7:
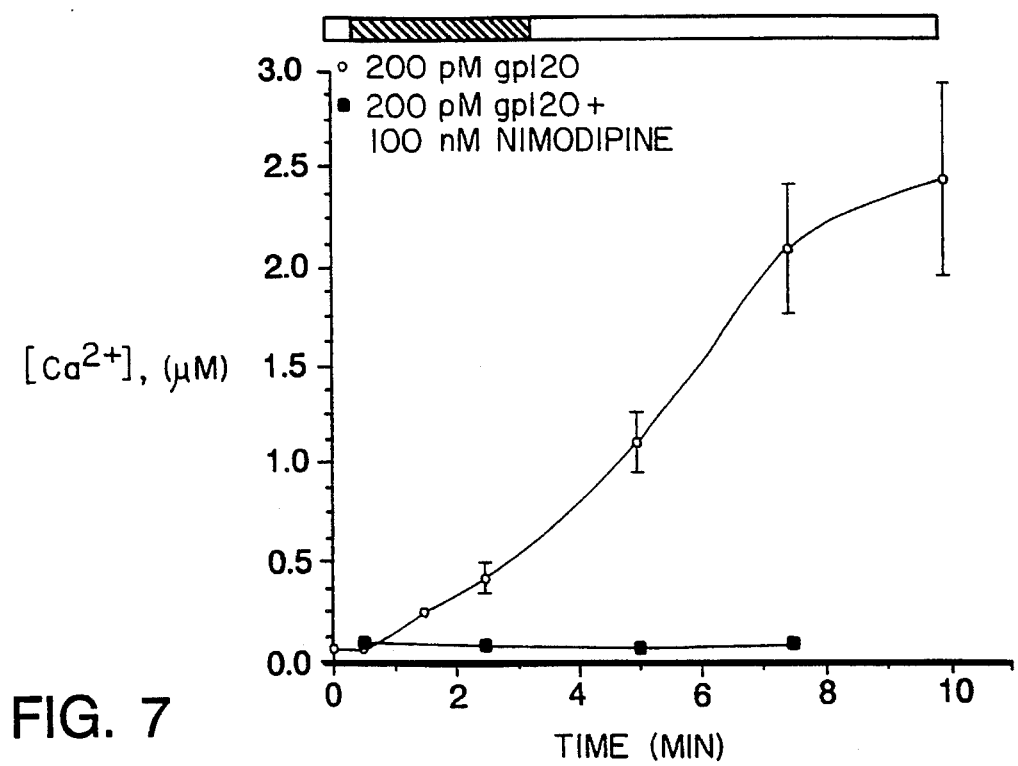
FIG. 7 is a graph of $[Ca^{2+}]i$ in the presence of gp120 and the $Ca^{2+}$ channel antagonist nimodipine.

FIG. 7 shows the effect of 100 nM nimodipine on the intracellular concentration of free $Ca^{2+}$ ions in retinal ganglion cells incubated with gp120. The cells were loaded with fura 2, as described above. The viral envelope protein gp120 (200 pM) was applied by puffer pipette to neurons previously bathed in normal medium or in medium containing 100 nM to 1 μM nimodipine for several min. For neurons bathed in normal calcium medium (O; n=10), gp120 produced an increase in [$Ca^{2+}$]i as expected. In contrast, after treatment with nimodipine (>; n=11), gp120 did not elicit a significant increase in [$Ca^{2+}$]i. Note that 5% serum is present in these cultures accounting for ~96% binding of nimodipine; thus the free (pharmacologically effective) dose of nimodipine is ~4% of the total concentration (e.g., ~4nM rather than 100 nM).

Current Flow in the Presence of gp120 is Inhibited by Antagonists of the Voltage Dependent Calcium Channel The following assay of neuronal cell function tests the effect of calcium channel antagonists on $Ca^{2+}$ ion flow through $Ca^{2+}$ channels. Without being bound to any theory as to the mechanism whereby gp120 increases cell death, it is possible that gp120 increases current flow across $Ca^{2+}$ channels. As a precautionary measure in screening for a compound capable of reducing the gp120-associated rise in intracellular $Ca^{2+}$ concentration, the following assay of $Ca^{2+}$ current should be performed in the presence of gp120.

Figure 8B:
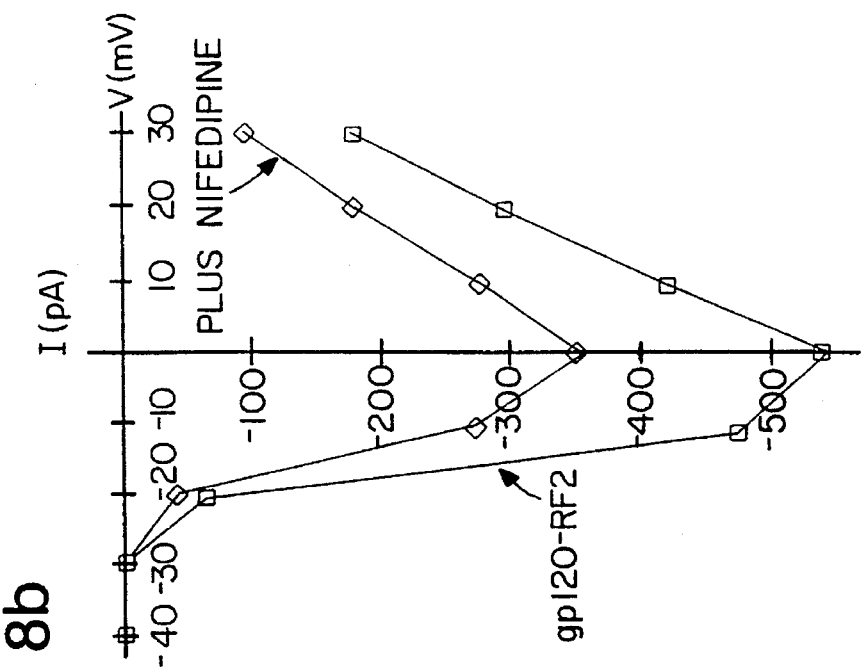
FIG. 8(a) shows current flowing through calcium channels in the presence of nifedipine and gp120, and (b) is a graph of the current-voltage relationship.
Figure 8A:
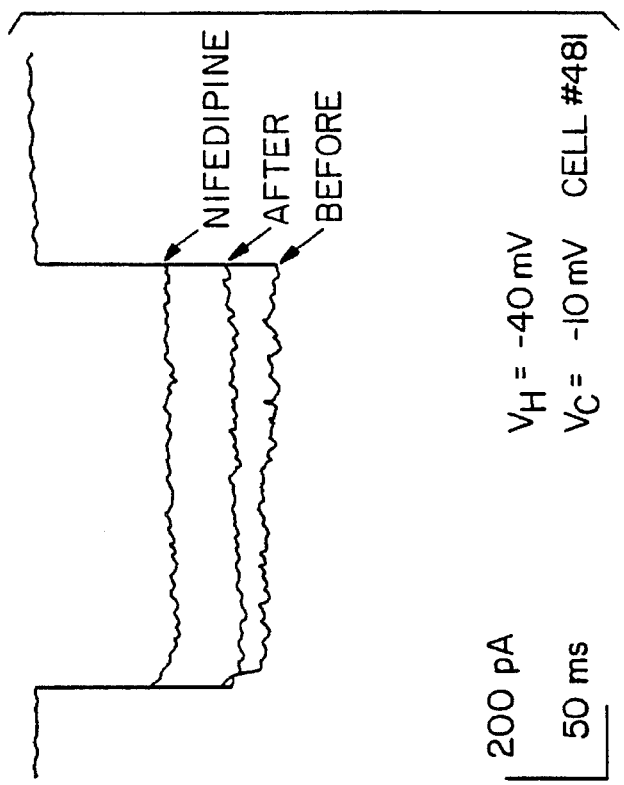
Figure 9:
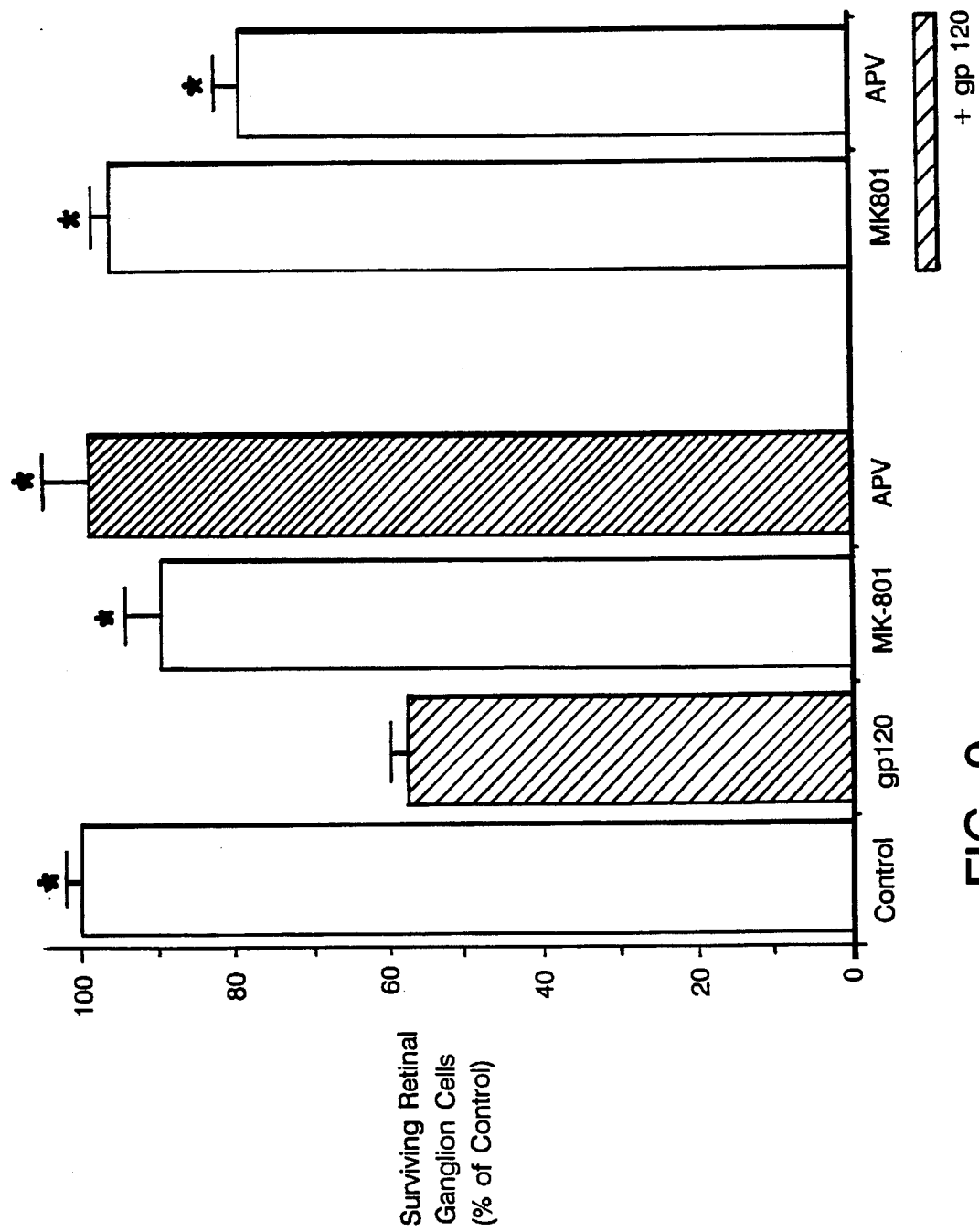
FIG. 9 is a graph of retinal cell survival in the presence of gp120 with or without 100 µM APV or 12 µM MK-801.

FIG. 8 shows that nifedipine suppresses $Ca^{2+}$ currents in the presence of gp120 in retinal ganglion cells. In FIG. 8a, in another neuron, nifedipine (10 μM) partially antagonized the current carried by $Ba^{2+}$ through calcium channels during the application of 20 pM gp120-RF2. All three traces were obtained in the presence of gp120. Inhibition by nifedipine was especially apparent (53% decrease) when the voltage step (in this case, $V_c$=−10 mV) was initiated from a depolarized holding potential ($V_H$=−40 mV); this observation is consistent with the action of dihydropyridine calcium channel blockers on $Ca^{2+}$ current in other tissues. FIG. 8b shows the I-V relationship for the same cell as in FIG. 8a, and illustrates the effect of nifedipine at various test potentials in the continued presence of 20 pM gp120-RF2. Recording conditions use barium as the charge-carrying species. A similar concentration range for antagonism of $Ca^{2+}$ current with nifedipine (100 nM–10μM) was obtained with nimodipine (100nM–10 M).

gp120-Promoted Cell. Death is Prevented by Antagonists of the NMDA Receptor-Channel Complex A specific NMDA receptor antagonist, D-2-amino-5-phosphonovalerate (APV), and a NMDA open-channel blocker, MK-801, both attenuate the lethal effect of recombinant gp120. Retinal ganglion cells from 1–2 week old Long Evans rats were isolated, identified, and cultured as described above. Treated cultures received either recombinant gp120 (produced and purified as described above) or recombinant gp120 and an antagonist at the time of plating. The ability of retinal ganglion cells to take up and cleave fluorescein diacetate to fluorescein was used as a measure of cell viability as described above. Cell viability was tested one day after treatment. Treatment with 100 μM APV or 12 μM MK-801 substantially increased the survival rate (FIG. 9). Statistical testing was performed as described above; at least 1200 retinal ganglion cells were counted in each experiment, which was then repeated 3 or more times.

NMDA Receptor-Channel Antagonists Block the Rise in Intracellular $[Ca^{2+}]$ Produced By gp120

Figure 10:
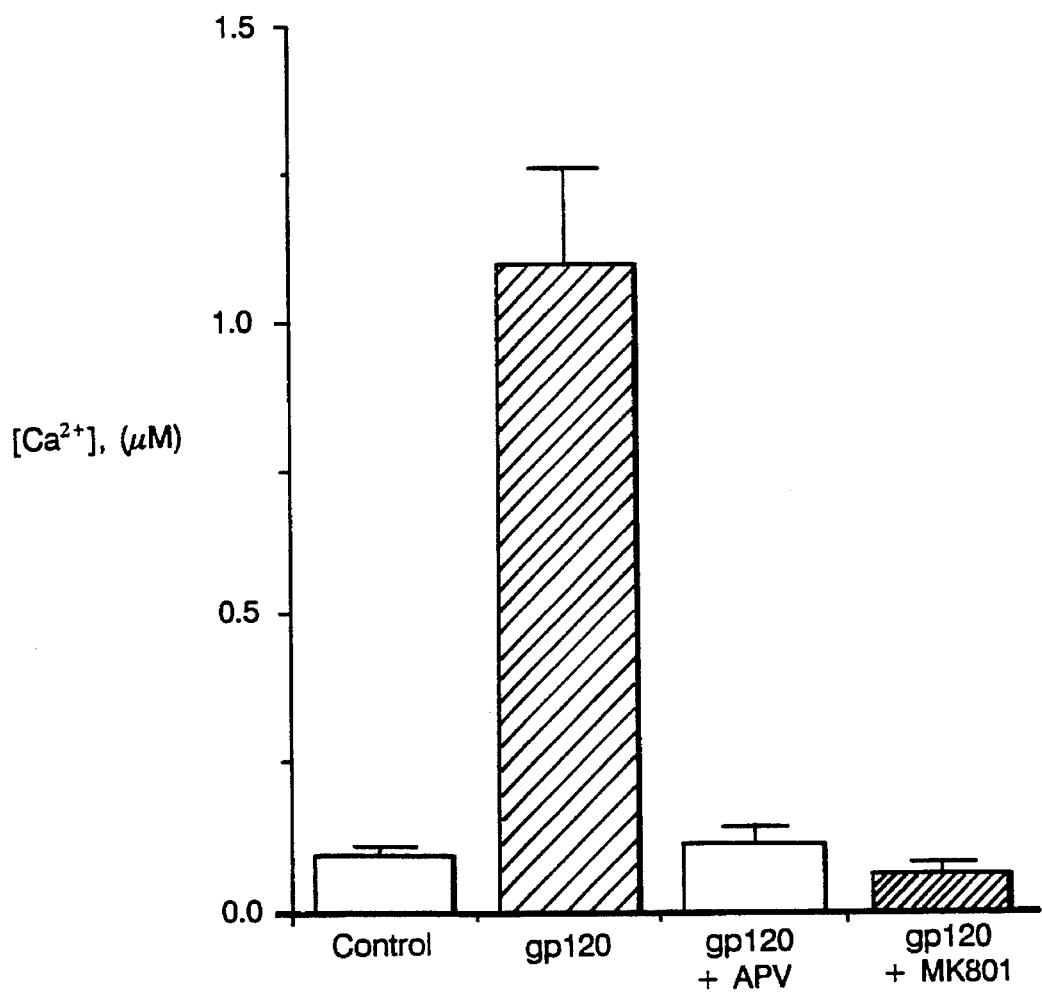
FIG. 10 is a graph of $[Ca^2+]i$ in the presence of 20 pM recombinant gp120 with or without 100 µM APV or 12 µM MK-801.

Retinal ganglion cells were prepared from the retina of 1–2 week old Long Evans rats as described above. After the cells were loaded with 10 μM fura-2, recombinant gp120 (20 pM) was mixed in the bathing solution in the presence or absence of an antagonist. The NMDA antagonists, APV (100 μM) and MK-801 (12 μM) were tested. Fluorescence digital imaging was performed as described above. As shown in FIG. 10, both antagonists attenuated the increase in intracellular $[Ca^{2+}]$ observed with gp120 alone.

Other Neurons are Sensitive to qp120

Another important consideration is whether or not $Ca^{2+}$ levels in mammalian central neurons other than retinal ganglion cells will be sensitive to gp120 and, therefore, amenable to treatment with calcium channel antagonists. Miller (*Science* 235:46, 1987) suggests that dihydropyridines affect $Ca^{2+}$ influx, at least to some degree, in over 90% of neurons from various brain areas; there were, however, regional differences in the effectiveness of these drugs. Other classes of calcium channel antagonists, such as phenylalkylamines, may prove effective in different areas of the brain. For example, the $Ca^{2+}$ current in hippocampal neurons has been shown to be partially suppressed by verapamil (100 μM) (Yaari et al., 1987, *Science* 235:680); in addition, novel calcium channel blockers or G proteins and intracellular messengers that affect their efficacy, may prove useful in this regard (Olivera et al., 1985, *Science* 230:338, Dolphin et al., 1987 *J. Physiol.* 386:1; and Yaari et al., 1987, *Science* 238:1288). Miller (supra) showed that hippocampal neurons were more sensitive to calcium channel antagonists than were striatal neurons. This variability can probably be attributed to the fact that only a prolonged component of $Ca^{2+}$ current (similar to L-type current) is sensitive to dihydropyridines. Use Antagonists of the invention may be administered by any one of a number of routes; for example, for a CNS-permeable antagonist such as nimodipine or Smith Kline drug no. 9512, nicardipine, flunarizine, or diproteverine, administration may be oral or intravenous, at a divided dosage of 60 to 1200 mg/day. MK-801 may be used at a daily dose of 0.01 to 0.2 mg/kg. For less CNS permeable antagonists, administration may be intrathecally or intravitreally, but oral or intravenous administration may be effective especially in the presence of break-down of the blood-brain barrier in sick patients; nifedipine is administered at a dosage of 20 to 800 mg/day; verapamil is administered at a dosage of 80 to 720 mg/day; and diltiazem is administered at a dosage of 60 to 960 mg/day. The effective daily dose of other drugs will range from 0.01 to 1000 mg/kg.

Other Embodiments

Other embodiments are within the following claims. For example, the method may be used for treatment of dementia, myelopathy, or vision loss associated with infection by a human immunodeficiency virus. The method can be used whether or not the patient manifests symptoms of the AIDS related complex or AIDS itself, and thus the method of the may be used as a prophylactic treatment for damage to CNS neurons, after HIV infection. In the method of the invention a useful compound may be administered by any means that allows the compound access to the central nervous system. The compounds useful in the method include antagonists of the voltage dependent calcium channel and of the NMDA receptor-channel complex that act to reduce the gp120-responsive rise in free $Ca^{2+}$ concentration in CNS neurons. The antagonists can prevent increases in free intracellular $Ca^{2+}$ by blocking the receptor channel, acting at a modulatory site or co-agonist site, or blocking the chain of events initiated by receptor activation. The method of the invention also includes administering to a single patient two of the useful compounds from multiple categories of modulators of intracellular $Ca^{2+}$ concentration.

I claim:

1. A method of reducing damage to a human patient's CNS neurons incident to infection of said patient with a human immunodeficiency virus (HIV), said method comprising administering to said patient a therapeutic composition comprising a compound which is an antagonist of the NMDA receptor-channel complex and which reduces the gp120-responsive rise in free $Ca^{++}$ ion concentration in said CNS neurons of said patient, in a concentration effective to cause such reduction.

2. The method of claim 1 wherein said compound is a competitive NMDA antagonist, acting at the agonist binding site.

3. The method of claim 1 wherein said compound is a un-competitive NMDA antagonist, blocking the NMDA channel.

4. The method of claim 1 wherein said compound is an NMDA antagonist operating at the glycine site of the NMDA receptor.

5. The method of claim 1 wherein said compound is an NMDA antagonist operating at the polyamine site of the NMDA receptor.

6. The method of claim 1 wherein said compound is an NMDA antagonist operating at the redox site of the NMDA receptor.

7. The method of claim 1 wherein said compound is a non-competitive NMDA antagonist.

8. The method of claim 1 wherein said compound inhibits protein kinase C activation by NMDA stimulation.

9. The method of claim 1 wherein said patient manifests symptoms of AIDS related complex or AIDS.

10. The method of claim 1 wherein said compound is administered orally or intravenously.

11. A method of reducing damage to a human patient's CNS neurons incident to infection of said patient with a human immunodeficiency virus (HIV), wherein the blood of said patient contains antibodies to HIV, said method comprising administering to said patient a therapeutic composition comprising a compound which is an antagonist of the NMDA receptor-channel complex and which will reduce the gp-120-responsive rise in free $Ca^{++}$ ion concentration in said CNS neurons of said patient, said administration being effective to cause such reduction.

12. A method of reducing damage to a human patient's CNS neurons incident to infection of said patient with a human immunodeficiency virus (HIV), said method comprising administering to said patient a therapeutic amount of an NMDA receptor complex antagonist selected from the group consisting of:
 a) MK-801 (dizocipline);
 b) dibenzocycloheptene;
 c) dextrorphan;
 d) dextromethorphan; and
 e) ketamine, said administration being effective to reduce said CNS damage incident to HIV infection of said patient.

13. The method of claim 12, wherein the compound is MK-801.

14. A method of reducing damage to a human patient's CNS neurons incident to infection of said patient with a human immunodeficiency virus (HIV), said method comprising administering to said patient an uncompetitive antagonist of the NMDA receptor channel complex, said administration being effective to reduce said CNS damage incident to HIV infection of said patient.

15. A method of treatment to reduce HIV-related vision loss, myelopathy or dementia in a human subject having an HIV infection, said method comprising administering an antagonist of the NMDA receptor-channel complex to said subject so as to reduce HIV-related vision loss, myelopathy or dementia.

16. A method of treatment to reduce HIV-related central nervous system damage in a human subject having an HIV infection, said method comprising administering an antagonist of the NMDA receptor-channel complex to said subject having an HIV infection, so as to reduce HIV-related central nervous system damage.

17. The method of claim 15 or claim 16 in which the antagonist is an NMDA receptor-channel complex antagonist that is not competitive.

* * * * *

UNITED STATES PATENT AND TRADEMARK OFFICE
CERTIFICATE OF CORRECTION

PATENT NO.    : 5,506,231
DATED         : APRIL 9, 1996
INVENTOR(S)   : STUART A. LIPTON

It is certified that error appears in the above-identified patent and that said Letters Patent is hereby corrected as shown below:

At column 1, line 22, before "BACKGROUND OF THE INVENTION" insert --This invention was made with government support under Grant No. RO1 EY09027 by the NIH. The government has certain rights in the invention.--

Signed and Sealed this

Twenty-sixth Day of September, 2000

Attest:

Q. TODD DICKINSON

*Attesting Officer*    *Director of Patents and Trademarks*